United States Patent
Aprikyan et al.

(10) Patent No.: US 9,675,708 B2
(45) Date of Patent: Jun. 13, 2017

(54) FUNCTIONALIZED NANOPARTICLES FOR INTRACELLULAR DELIVERY OF BIOLOGICALLY ACTIVE MOLECULES

(71) Applicant: STEMGENICS, INC, Seattle, WA (US)

(72) Inventors: Andranik Andrew Aprikyan, Seattle, WA (US); Kilian Dill, Sultan, WA (US)

(73) Assignee: Stemgenics, Inc., Kenmore, WA (US)

( * ) Notice: Subject to any disclaimer, the term of this patent is extended or adjusted under 35 U.S.C. 154(b) by 0 days.

(21) Appl. No.: 14/353,280

(22) PCT Filed: Oct. 22, 2012

(86) PCT No.: PCT/US2012/061391
§ 371 (c)(1),
(2) Date: Apr. 21, 2014

(87) PCT Pub. No.: WO2013/059831
PCT Pub. Date: Apr. 25, 2013

(65) Prior Publication Data
US 2014/0342004 A1    Nov. 20, 2014

Related U.S. Application Data

(60) Provisional application No. 61/550,213, filed on Oct. 21, 2011.

(51) Int. Cl.
*A61K 47/48* (2006.01)
*A61K 38/02* (2006.01)
*B60R 22/34* (2006.01)
*B60R 22/28* (2006.01)

(52) U.S. Cl.
CPC ........ *A61K 47/48892* (2013.01); *A61K 38/02* (2013.01); *B60R 22/3413* (2013.01); *B60R 2022/286* (2013.01); *B60R 2022/289* (2013.01)

(58) Field of Classification Search
None
See application file for complete search history.

(56) References Cited

U.S. PATENT DOCUMENTS

| 8,283,344 | B2 | 10/2012 | Dale et al. | |
|---|---|---|---|---|
| 2005/0042753 | A1 | 2/2005 | Yang | |
| 2006/0251726 | A1* | 11/2006 | Lin | A61K 9/127 424/489 |
| 2008/0166412 | A1 | 7/2008 | Sugaya et al. | |
| 2008/0213377 | A1* | 9/2008 | Bhatia | A61K 47/48238 424/489 |
| 2009/0226372 | A1 | 9/2009 | Ruoslahti et al. | |
| 2010/0298536 | A1 | 11/2010 | Park et al. | |
| 2011/0059960 | A1 | 3/2011 | Dale et al. | |
| 2011/0190729 | A1 | 8/2011 | Kirkland et al. | |

FOREIGN PATENT DOCUMENTS

| CN | 101389314 A | 3/2009 |
|---|---|---|
| WO | 2009014404 A2 | 1/2009 |
| WO | 2009035541 A1 | 3/2009 |

OTHER PUBLICATIONS

Zhou et al. Cell Stem Cell. 4;381-384, 2009.*
Agemy et al., Targeted Nanoparticle enhanced proapoptotic peptide as potential therapy for glioblastoma, PNAS, Oct. 18, 2011, pp. 17450-17455, vol. 106, Iss. 42.
Josephson et al., High-Efficiency Intracellular Magnetic Labeling with Novel Superparamagnetic-Tat Peptide Conjugates, Bioconjugate Chem., 1999, pp. 186-191, vol. 10, Iss. 2.
Laurent et al., Superparamagnetic iron oxide nanoparticles: promises for diagnosis and treatment of cancer, Int J Mol Epidemiol Genet, 2011, pp. 367-390, vol. 2, Iss. 4.
Veiseh et al., Design and fabrication of magnetic nanoparticles for targeted drug delivery and imaging, Advanced Drug Delivery Reviews, 2010, pp. 284-304, vol. 62, Elsevier.
Xie et al., Nanoparticle-based theranostic agents, Advanced Drug Delivery Reviews, 2010, pp. 1064-1079, vol. 62, Elsevier.
Extended European Search Report, Application No. EP 12 84 2115, dated May 6, 2015.
Extended European Search Report, Application No. EP 12 84 2115, dated Apr. 20, 2015.
International Search Report and Written Opinion, PCT/US12/61391, mailed Dec. 28, 2012, 2 pages.
Written Opinion of Singapore Patent Application No. 11201401658S dated Mar. 5, 2015.
Office Action from Chinese Patent Application No. 201280063870.2 dated Jun. 2, 2015.
Office Action from Canadian Patent Application No. 2,853,128 dated Mar. 17, 2015.
Aprikyan et al., Impaired survival of bone marrow hematopoietic progenitor cells in cyclic neutropenia, Blood, 2001, 147-153, vol. 97, Iss. 1.
Aprikyan et al., Cellular and molecular abnormalities in severe congenital neutropenia predisposing to leukemia, Experimental Hematology, 2003, 372-381, vol. 31.

(Continued)

*Primary Examiner* — Amber D Steele
(74) *Attorney, Agent, or Firm* — Myles Intellectual Property Law PS; Gary M. Myles (57) ABSTRACT

Functionalized biocompatible nanoparticles capable of penetrating through a mammalian cell membrane and delivering intracellularly a plurality of bioactive molecules for modulating a cellular function are disclosed herein The functionalized biocompatible nanoparticles comprise: a central nanoparticle ranging in size from about 5 to about 50 nm and having a polymer coating thereon, a plurality of functional groups covalently attached to the polymer coating, wherein the plurality of bioactive molecules are attached to the plurality of the functional groups, and wherein the plurality of bioactive molecules include at least a peptide and a protein, and wherein the peptide is capable of penetrating through the mammalian cell membrane and entering into the cell, and wherein the protein is capable of providing a new functionality within the cell. The protein may be a transcription factor selected from the group consisting of Oct4, Sox2, Nanog, Lin28, cMyc, and Klf4.

14 Claims, 6 Drawing Sheets

(56) References Cited

OTHER PUBLICATIONS

Carlsson et al., Kostmann syndrome: severe congenital neutropenia associated with defective expression of Bcl-2, constitutive mitochondrial release of cytochrome c, and excessive apoptosis of myeloid progenitor cells, Blood, 2004, 3355-3361, vol. 103, Iss. 9.
Dale et al., Mutations in the gene encoding neutrophil elastase in congenital and cyclic neutropenia, Blood, 2000, 2317-2322, vol. 96, Iss. 7.
Devriendt et al., Constitutively activating mutation in WASP causes Xlinked severe congenital neutropenia, Nature Genetics, 2001, 313-317, vol. 27 (Abstract).
Harisinghani et al., MR lymphangiography using ultrasmall superparamagnetic iron oxide in patients with primary abdominal and pelvic malignancies: radiographic-pathologic correlation, Am. J. Roentgenol., 1999, 1347-51, vol. 172, Iss. 5 (Abstract).
Klein, HAX1 deficiency causes autosomal recessive severe congenital neutropenia (Kostmann disease), Nat Genet, 2007, 86-92, vol. 39 (Abstract).
Lewin et al., Tat peptide-derivatized magnetic nanoparticles allow in vivo tracking and recovery of progenitor cells, Nature Biotechnology, 2000, 410-414, vol. 19.
Makaryan et al., The cellular and molecular mechanisms for neutropenia in Barth syndrome, Eur J Haematol., 2012, 195-209, vol. 88, Iss. 3.
Mishra et al., Translocation of HIV TAT peptide and analogues induced by multiplexed membrane and cytoskeletal interactions, PNAS, Oct. 11, 2011, 6883-16888, vol. 108, Iss. 41.
Moretti et al., Mouse and human induced pluripotent stem cells as a source for multipotent Isl1+ cardiovascular progenitors, Faseb J, 2010, 700-711, vol. 24.
Newberger et al., Cyclic Neutropenia and Severe Congenital Neutropenia in Patients With a Shared ELANE Mutation and Paternal Haplotype: Evidence for Phenotype Determination by Modifying Genes, Pediatr Blood Cancer, 2010, 314-317, vol. 55.
Park et al., Reprogramming of human somatic cells to pluripotency with defined factors, Nature, 2008, 141-147, vol. 451.
Rosenberg et al., Neutrophil elastase mutations and risk of leukaemia in severe congenital neutropenia, Br J Haematol., 2008, 210-213, vol. 140, Iss. 2.
Shen et al., Monocrystalline iron oxide nanocompounds (MION): physicochemical properties, Magn Reson Med., 1993, 599-604, vol. 29, Iss. 5 (Abstract).
Sniadecki, Minireview: A Tiny Touch: Activation of Cell Signaling Pathways with Magnetic Nanoparticles, Endocrinology, 2010, 451-457, vol. 151, Iss. 2.
Soldner et al., Parkinson's Disease Patient-Derived Induced Pluripotent Stem CellsFree of Viral Reprogramming Factors, Cell, 2009, 964-977, vol. 136.
Takahashi et al., Induction of Pluripotent Stem Cells from Adult Human Fibroblasts, Cell, 2007, 861-872, vol. 131.
Thier et al., Cellular Reprogramming Employing Recombinant Sox2 Protein, Stem Cells International, 2012, 1-10, vol. 2012.
Warren et al., Highly Efficient Reprogramming to Pluripotency and Directed Differentiation of Human Cells with Synthetic Modified mRNA, Cell Stem Cell, 2010, 618-630, vol. 7.
Weissleder et al., Superparamagnetic Iron Oxide: Pharmacokinetics and Toxicity, AJR, 1989, 167-173, vol. 152.
Welte and Dale, Pathophysiology and treatment of severe chronic neutropenia, Annals of Hematology, 1996, 158-165, vol. 72, Iss. 4 (Abstract).
Woltjen et al., PiggyBac transposition reprograms fibroblasts to induced pluripotent stem cells, Nature, 2009, 766-771, vol. 458.
Yadav et al., Development of peptide and protein nanotherapeutics by nanoencapsulation and nanobioconjugation, Peptides, 2011, 173-187, vol. 32.
Yu et al., Human Induced Pluripotent Stem Cells Free of Vector and Transgene Sequences, Science, 2009, 797-801, vol. 324, Iss. 5928.
Zhou et al., Generation of Induced Pluripotent Stem Cells Using Recombinant Proteins, Cell Stem Cell, 2009, 381-384, vol. 4.

\* cited by examiner

FUNCTIONALIZED NANOPARTICLES FOR INTRACELLULAR DELIVERY OF BIOLOGICALLY ACTIVE MOLECULES

CROSS-REFERENCE TO RELATED APPLICATIONS

This U.S. non-provisional patent application was filed on Apr. 21, 2014 as a 371 of PCT Patent Application No. PCT/US12/61391, which was filed on Oct. 22, 2012 and claims the benefit of U.S. Provisional Patent Application No. 61/550,213, which was filed on Oct. 21, 2011. The entirety of PCT Patent Application No. PCT/US12/61391 and U.S. Provisional Patent Application No. 61/550,213 is incorporated by reference herein.

TECHNICAL FIELD

The present invention relates generally to organic synthesis and nanobiotechnology, and, more particularly, to functionalized nanoparticles for the delivery of bioactive molecules into cells for modulation of cellular function, as well as to methods related thereto.

BACKGROUND OF THE INVENTION

The ability of cells to normally proliferate, migrate and differentiate to various cell types is critical in embryogenesis and in the function of mature cells, including but not limited to the cells of hematopoietic and/or cardiovascular systems in a variety of inherited or acquired diseases. This functional ability of stem cells and/or more differentiated specialized cell types is altered in various pathological conditions, but can be normalized upon intracellular introduction of biologically active components. For example, abnormal cellular functions such as impaired survival and/or differentiation of bone marrow stem/progenitor cells into neutrophils are observed in patients with cyclic or severe congenital neutropenia who may suffer from severe life-threatening infections and may evolve to develop acute myelogenous leukemia or other malignancies [Aprikyan et al., Impaired survival of bone marrow hematopoietic progenitor cells in cyclic neutropenia. Blood, 97, 147 (2001); Goran Carlsson et al., Kostmann syndrome: severe congenital neutropenia associated with defective expression of Bcl-2, constitutive mitochondrial release of cytochrome C, and excessive apoptosis of myeloid progenitor cells. Blood, 103, 3355 (2004)]. Inherited or acquired disorders such as severe congenital neutropenia or Barth syndrome are triggered by various gene mutations and are due to deficient production and function of patients' blood and/or cardiac cells leading to subsequent neutropenia, cardiomyopathy and/or heart failure [Makaryan et al., The cellular and molecular mechanisms for neutropenia in Barth syndrome. Eur J Haematol. 88:195-209 (2012)]. Severe congenital neutropenia disease phenotype can be caused by different substitution, deletion, insertion or truncation mutations in the neutrophil elastase gene, HAX1 gene, or Wiskott-Aldrich Syndrome Protein gene [Dale et al., Mutations in the gene encoding neutrophil elastase in congenital and cyclic neutropenia. *Blood.* 96:2317-2322 (2000); Devriendt et al., Constitutively activating mutation in WASP causes X-linked severe congenital neutropenia. *Nat Genet.* 27:313-7 (2001); Klein et al., HAX1 deficiency causes autosomal recessive severe congenital neutropenia (Kostmann disease) *Nat Genet.* 39:86-92 (2007)].

Other inherited diseases like Barth syndrome, a multisystem stem cell disorder induced by presumably loss-of-function mutations in the mitochondrial TAZ gene is associated with neutropenia (reduced levels of blood neutrophils) that may cause recurring severe and sometimes life-threatening fatal infections and/or cardiomyopathy that may lead to heart failure that could be resolved by heart transplantation. In most of the cases, the mutant gene products, implicated in pathogenesis and development of inherited or acquired human diseases, affect distinct intracellular events, which lead to abnormal cellular functions and the specific disease phenotype.

Treatment of these patients with granulocyte colony-stimulating factor (G-CSF) induces conformational changes in the G-CSF receptor molecule located on the cell surface, which subsequently triggers a chain of intracellular events that eventually restores the production of neutrophils to near normal level and improves the quality of life of the patients [Welte and Dale. Pathophysiology and treatment of severe chronic neutropenia. Ann. Hematol. 72, 158 (1996)]. Nevertheless, patients treated with G-CSF may evolve to develop leukemia [Aprikyan et al., Cellular and molecular abnormalities in severe congenital neutropenia predisposing to leukemia. Exp Hematol. 31, 372 (2003); Philip Rosenberg et al., Neutrophil elastase mutations and risk of leukaemia in severe congenital neutropenia. Br J Haematol. 140, 210 (2008); Peter Newburger et al., Cyclic Neutropenia and Severe Congenital Neutropenia in Patients with a Shared ELANE Mutation and Paternal Haplotype: Evidence for Phenotype Determination by Modifying Genes. Pediatr. Blood Cancer, 55, 314 (2010)], which is why novel alternative approaches are being explored.

The intracellular events can be more effectively affected and regulated upon intracellular delivery of different biologically active molecules using distinctly functionalized nanoparticles. These bioactive molecules may normalize the cellular function or may eliminate the unwanted cells when needed. However, the cellular membrane serves as an active barrier preserving the cascade of intracellular events from being affected by exogenous stimuli.

Accordingly, there is a need in the art for new types of bioactive molecules that are capable of penetrating cellular membranes and effectuating the intracellular events of interest. The present invention fulfills these needs and provides for further related advantages.

SUMMARY OF THE INVENTION

The present invention in some embodiments is directed to functionalization methods of linking proteins and/or peptides to biocompatible nanoparticles for modulating cellular functions. In some embodiments, the present invention is directed to the functionalized biocompatible nanoparticles themselves.

In an embodiment, a functionalized biocompatible nanoparticle capable of penetrating through a mammalian cell membrane and delivering intracellularly a plurality of bioactive molecules for modulating a cellular function, comprises: a central nanoparticle ranging in size from 5 to 50 nm and having a polymer coating thereon, a plurality of functional groups covalently attached to the polymer coating, wherein the plurality of bioactive molecules are attached to the plurality of the functional groups, and wherein the plurality of bioactive molecules include at least a peptide and a protein, and wherein the peptide is capable of penetrating through the mammalian cell membrane and entering into the cell, and wherein the protein is capable of providing a new functionality within the cell.

The central nanoparticle may comprise iron and be magnetic. The peptides of the present invention may be attached to the protein (as opposed to being attached to the nanoparticle). The peptides and proteins may each be attached to the nanoparticle by way of one or more interposing linker molecules. The peptide may include five to nine basic amino acids in some embodiments, whereas in other embodiments the peptide includes nine or more basic amino acids. The protein may be a transcription factor such as, for example, a transcription factor selected from the group consisting of Oct4, Sox2, Nanog, Lin28, cMyc, and Klf4.

In another aspect, the present invention is directed to a method of changing a cellular functionality within a mammalian cell. The novel method comprises administering an effective amount of functionalized biocompatible nanoparticles to the cell and changing the cellular functionality within the cell. The changing of the cellular functionality may involve a change in a physico-chemical property of the cell, a change in proliferative property of the cell, a change in surviving ability of the cell, or a change in morphological phenotypical property of the cell. The changing of the cellular functionality may involve an acquired ability of the cell to make a new cell type including a stem cell or a more specialized cell type.

These and other aspects of the present invention will become more evident upon reference to the following detailed description and attached drawings. It is to be understood, however, that various changes, alterations, and substitutions may be made to the specific embodiments disclosed herein without departing from their essential spirit and scope. Finally, all of the various references cited herein are expressly incorporated herein by reference.

These and other aspects of the present invention will become more readily apparent to those possessing ordinary skill in the art when reference is made to the following detailed description in conjunction with the accompanying drawings.

DETAILED DESCRIPTION OF THE INVENTION

In order to deliver biologically active molecules intracellularly, the inventors of the present invention present a universal device based on cell membrane-penetrating nanoparticles with covalently linked biologically active molecules. To this end, the inventors present herein a novel functionalization method that ensures a covalent linkage of proteins and peptides to nanoparticles. The modified cell-permeable nanoparticles of the present invention provide a universal mechanism for intracellular delivery of biologically active molecules for regulation and/or normalization of cellular function.

The ability of cells to normally proliferate, migrate and differentiate to various cell types is critical in embryogenesis and in the function of mature cells, including but not limited to the stem/progenitor and more differentiated cells of hematopoietic and cardiovascular systems in a variety of inherited or acquired diseases. This functional ability of stem cells and/or more differentiated specialized cell types is altered in various pathological conditions due to aberrant alterations in intracellular events, but can be normalized upon intracellular introduction of biologically active components. For example, the impaired survival and differentiation of human bone marrow progenitor cells into neutrophils that is observed in patients with cyclic or severe congenital neutropenia who suffer from severe life-threatening infections and may evolve to develop leukemia, may be normalized by cell membrane-penetrant small molecule inhibitor of neutrophil elastase, which interferes with aberrant intracellular events and apparently restores the normal phenotype. Nevertheless, such small molecules specific to target mutant products causing the disease are rarely available which is why alternative efficient cell membrane-penetrant devices are needed for intracellular delivery of biologically active molecules capable of modulating cellular function.

The methods disclosed herein utilize biocompatible nanoparticles, including for example, superparamagnetic iron oxide particles similar to those previously described in scientific literature. This type of nanoparticles can be used in clinical settings for magnetic resonance imaging of bone marrow cells, lymph nodes, spleen and liver [see, e.g., Shen et al., Monocrystalline iron oxide nanocompounds (MION); physicochemical properties. Magn. Reson. Med., 29, 599 (1993); Harisinghani et. al., MR lymphangiography using ultrasmall superparamagnetic iron oxide in patients with primary abdominal and pelvic malignancies. Am. J. Roentgenol. 172, 1347 (1999)]. These magnetic iron oxide nanoparticles contain ~5 nm nucleus coated with cross-linked dextran and having ~45 nm overall particle size. Importantly, it has been demonstrated that these nanoparticles containing cross-linked cell membrane-permeable Tat-derived peptide efficiently internalize into hematopoietic and neural progenitor cells in quantities of up to 30 pg of superparamagnetic iron nanoparticles per cell [Lewin et al., Tat peptide-derivatized magnetic nanoparticles allow in vivo tracking and recovery of progenitor cells. Nat. Biotechnol. 18, 410 (2000)]. Furthermore, the nanoparticle incorporation does not affect proliferative and differentiation characteristics of bone marrow-derived CD34+ primitive progenitor cells or the cell viability [Maite Lewin et al., Nat. Biotechnol. 18, 410 (2000)]. These nanoparticles can be used for in vivo tracking the labeled cells.

The labeled cells retain their differentiation capabilities and can also be detected in tissue samples using magnetic resonance imaging. Here we present novel nanoparticle-based devices which are now functionalized to carry peptides and proteins that can serve as excellent vehicles for intracellular delivery of biologically active molecules for cell reprogramming solutions to target intracellular events and modulate cellular function and properties.

General Description of Nanoparticle-Peptide/Protein Conjugates:

Nanoparticles based on iron or other material with biocompatible coating (e.g. dextran polisaccharide) with X/Y functional groups, to which linkers of various lengths are attached, which, in turn are covalently attached to proteins and/or peptides (or other small molecules) through their X/Y functional groups.

Functional groups that may be used for crosslinking include:
—$NH_2$ (e.g., lysine, a-$NH_2$),
—SH,
—COOH,
—NH—C(NH)($NH_2$),
carbohydrate,
-hydroxyl (OH),
-attachment via photochemistry of an azido group on the linker.

Crosslinking reagents may include:
SMCC [succinimidyl 4-(N-maleimido-methyl)cyclohexane-1-carboxylate] Also available is Sulfo-SMCC, the Sulfosuccinimidylderivative for crosslinking amino and thiol groups.
LC-SMCC (Long chain SMCC). Also Sulfo-LC-SMCC.
SPDP [N-Succinimidyl-3-(pypridyldithio)-proprionate] Also Sulfo-SPDP. Reacts with amines and provides thiol groups.
LC-SPDP (Long chain SPDP). Also Sulfo-LC-SPDP.
EDC [1-Ethyl Hydrocholride-3-(3-Dimethylaminopropyl)carbodiimide] Reagent used to link —COOH group with —$NH_2$ group.
SM(PEG)n where n=1, 2, 3, 4 . . . 24 glycol units. Also the Sulfo-SM(PEG)n derivative.
SPDP(PEG)n where n=1, 2, 3, 4 . . . 12 glycol units. Also the Sulfo-SPDP(PEG)n derivative.
PEG molecule containing both carboxyl and amine groups.
PEG molecule containing both carboxyl and sulfhydryl groups.

Capping and blocking reagents include:
Citraconic Anhydride—specific for NH
Ethyl Maleimide—specific for SH
Mercaptoethanol—specific for maliemide In view of the foregoing, we have treated biocompatible nanoparticles to produce functional amines on the surface, which in turn were used to chemically bind proteins and short peptides.

In the case of attaching proteins, for example Green Fluorescent Protein or a transcription factor, to superparamagnetic or alternative nanoparticles, the following protocol can be used: Superparamagnetic beads containing amino functional groups on the exterior can be commercially purchased from various manufacturers. They can range from 20-50 nm in size and $10^{15}$-$10^{20}$ nanoparticles per ml with 10 or more amine groups per nanoparticle. The nanoparticles are placed into the correct reaction buffer (0.1 M phosphate buffer, pH 7.2) by use of an Amicon centrifugal filter unit (microcolumn) with a molecular cutoff of 10,000 dalton. Approximately 4 washes are generally required to ensure proper buffering system. Nanoparticles are removed from the filter unit as recommended by manufacturer (inverting column/filter device by spinning at low speed).

SMCC (from Thermo Fisher) was dissolved in dimethylformamide (DMF) obtained from ACROS (sealed vial and anhydrous) at the 1 mg/ml concentration. Sample is sealed and used almost immediately.

Ten (10) microliters of the solution are added to nanoparticles in 200 microliter volume. This provides a large excess of SMCC to the available amine groups present, and the reaction is allowed to proceed for one hour. Excess SM and DMF can be removed using an Amicon centrifugal filter column with a cutoff of 3,000 daltons. Five exchanges of volume are generally required to ensure proper buffer exchange. It is important that excess of SMCC be removed at this stage.

Any peptide based molecule, as an example commercially available Green Fluorescent Protein (GFP) or purified recombinant GFP or other proteins are added to the solution containing a certain amount of ethylene glycol for freezing at −30° C. To 3 micrograms of the protein in 14 microliters, 10 microliters of a freshly prepared DTT (dithiothreitol, Cleland's reagent) solution in PBS are added with vigorous vortexing. Because the proteins usually contain more than one cysteine, there is a tendency to crosslink different GFP molecules. Therefore, the excess DTT reduces the dithiol linkage and frees GFP. Reaction is allowed to proceed for two hours at 4° C. and then excess reagent is removed by an Amicon centrifugal filter unit with a 3,000 MW cutoff.

The activated nanoparticles and the protein solutions are combined and allowed to react for two hours, after which the unreacted protein is removed by an Amicon centrifugal filter unit having an appropriate MW cutoff (in the example with GFP it is 50,000 dalton cut-off). Sample is stored at −80° C. Instead of using Amicon spin filter columns, small spin columns containing solid size filtering components, such as Bio Rad P columns can also be used. These are size exclusion columns. It should also be noted that SMCC also can be purchased as a sulfo derivative (Sulfo-SMCC), making it more water soluble. DMSO may also be substituted for DMF as the solvent carrier for the labeling reagent; again, it should be anhydrous.

All the other crosslinking reagents can be applied in a similar fashion. SPDP is also applied to the protein/applicable peptide in the same manner as SMCC. It is readily soluble in DMF. The dithiol is severed by a reaction with DTT for an hour or more. After removal of byproducts and unreacted material, it is purified by use of an Amicon centrifugal filter column with 3,000 MW cutoff.

Another more direct and controlled means of labeling a nanoparticle with a peptide and protein would be to use two different bifunctional coupling reagents. The reaction sequence is somewhat similar to that of FIG. 1. Iodoacetic acid is used to introduce a select number of "carboxyl" groups on the nanoparticle surface.

Figure 1:
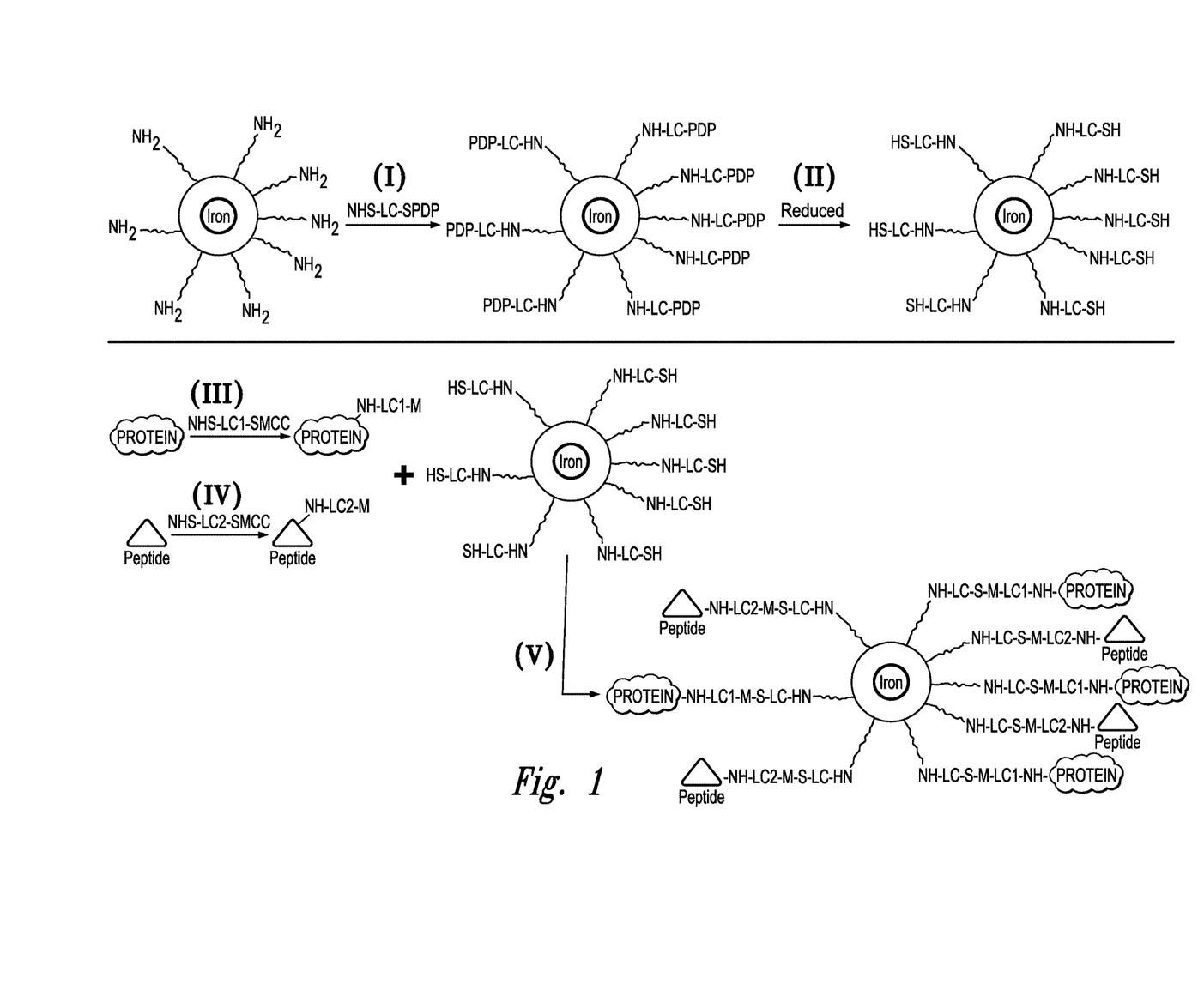
FIG. 1 depicts a multi-step functionalization of nanoparticles scheme based on the simultaneous attachment of peptide and protein molecules to a nanoparticle in accordance with an embodiment of the present invention.
Figures 2A, 2B:
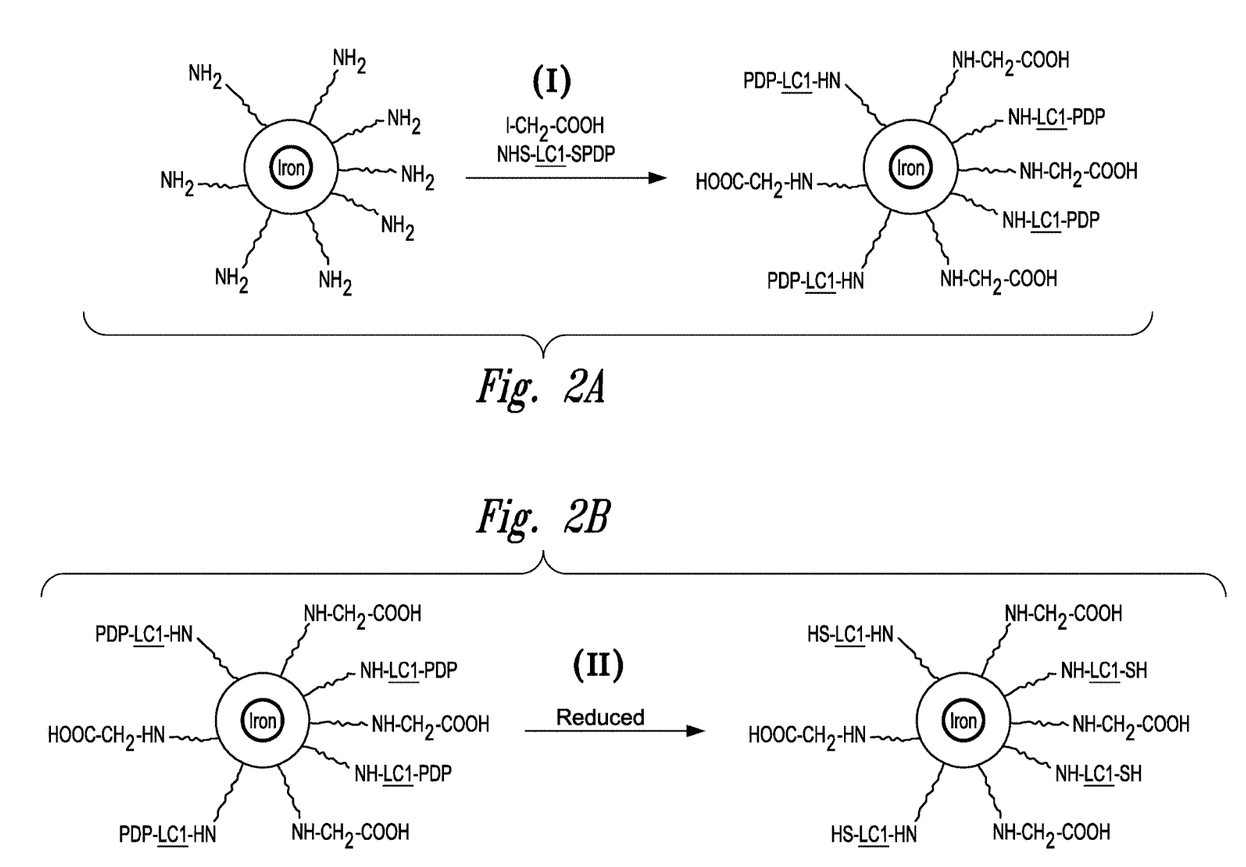
FIG. 2A depicts a reaction of a nanoparticle containing amine groups with equimolar ratios of long chain LC1-SPDP and Iodoacetic acid nanoparticle in accordance with an embodiment of the present invention.
FIG. 2B depicts a reduction of the disulfide bond of PDP to provide a free SH group nanoparticle in accordance with an embodiment of the present invention.
Figure 2C:
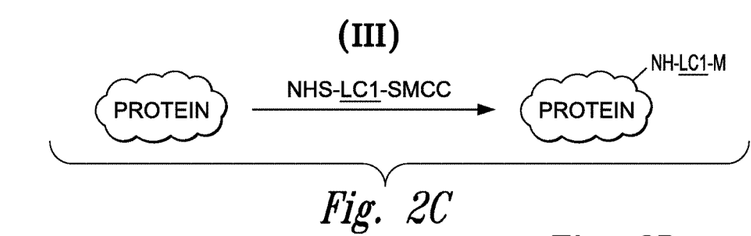
FIG. 2C depicts a reaction of long chain LC1-SMCC with the lysine groups of a protein nanoparticle in accordance with an embodiment of the present invention.
Figure 2D:
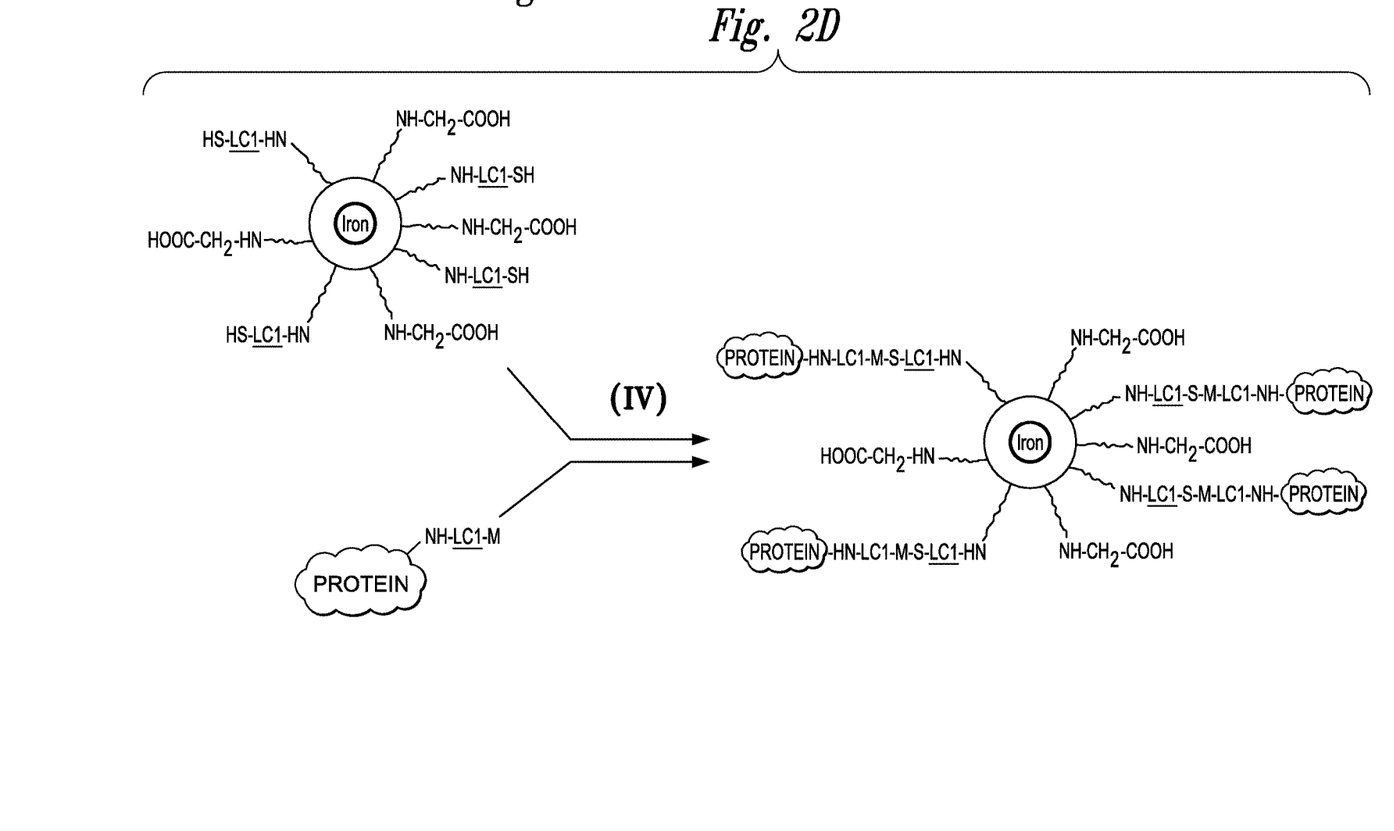
FIG. 2D depicts a reaction of a multifunctional nanoparticle with the protein that had been reacted with SMCC and contains a terminal reactive maleimide group nanoparticle in accordance with an embodiment of the present invention.
Figures 2E, 2F:
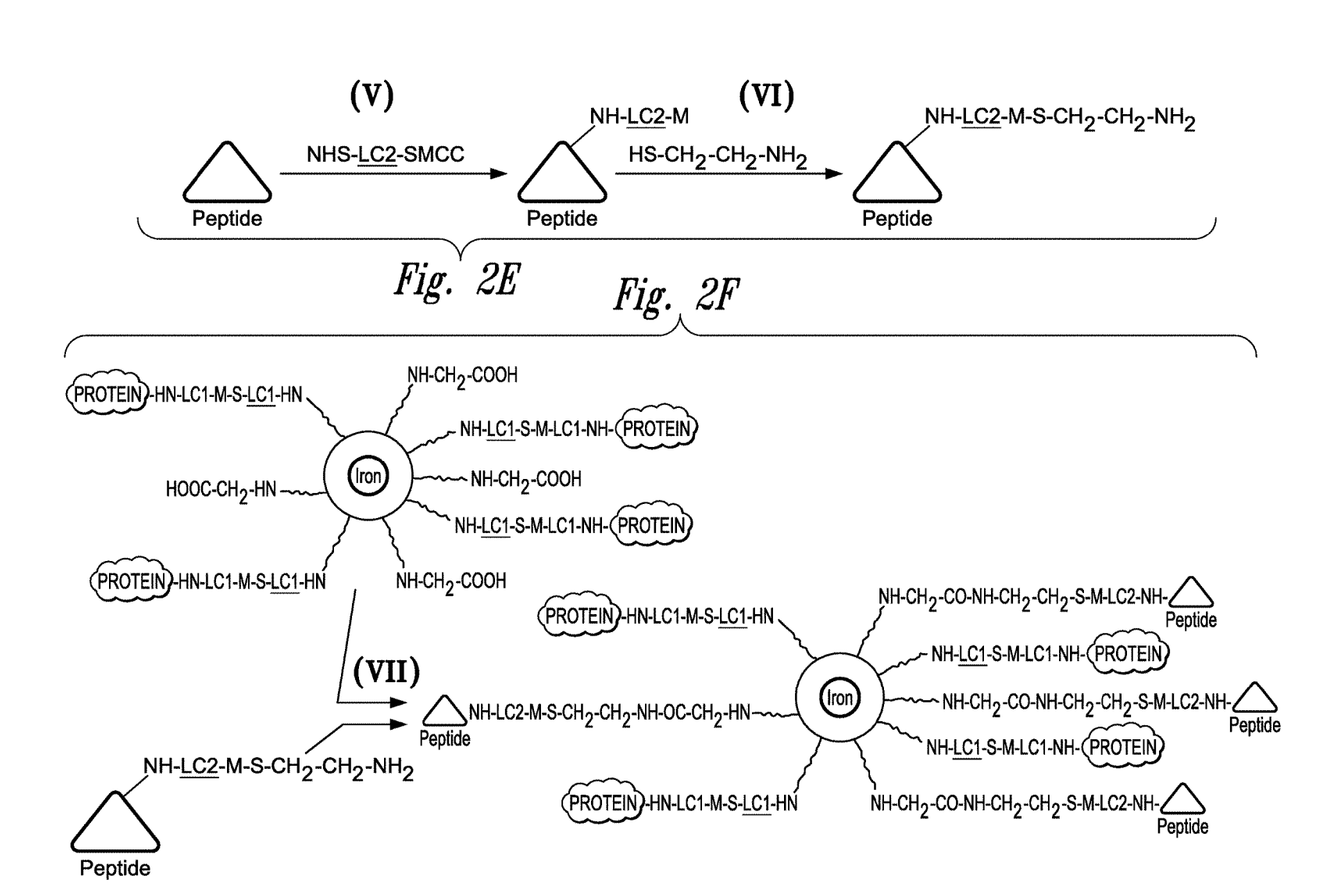
FIG. 2E depicts a reaction of an amino group of a peptide with LC2-SMCC. The reaction is then subsequently followed by a reaction with mercaptoethanol to convert the terminal maleimide to an alcohol nanoparticle in accordance with an embodiment of the present invention.
FIG. 2F depicts a reaction of a functional bead (and protein attached) with a modified peptide to the free carboxyl group on the nanoparticle nanoparticle in accordance with an embodiment of the present invention.
Figure 3A:
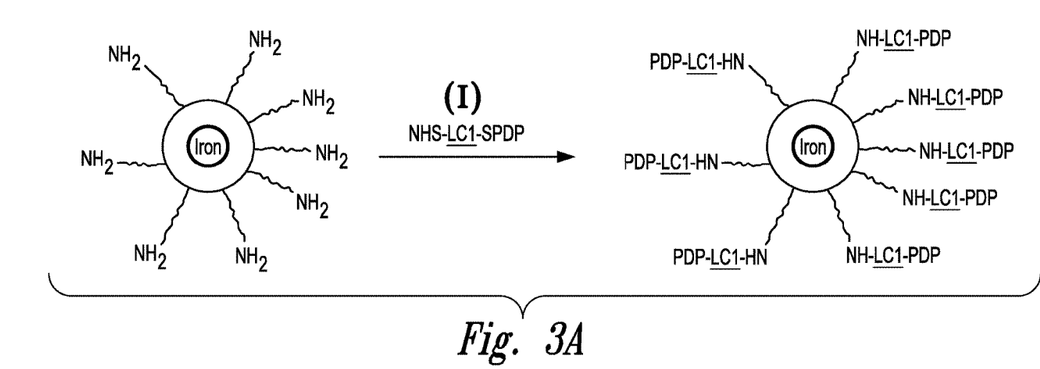
FIG. 3A depicts a reaction of a nanoparticle containing amine groups with LC1-SPDP nanoparticle in accordance with an embodiment of the present invention.
Figure 3B:
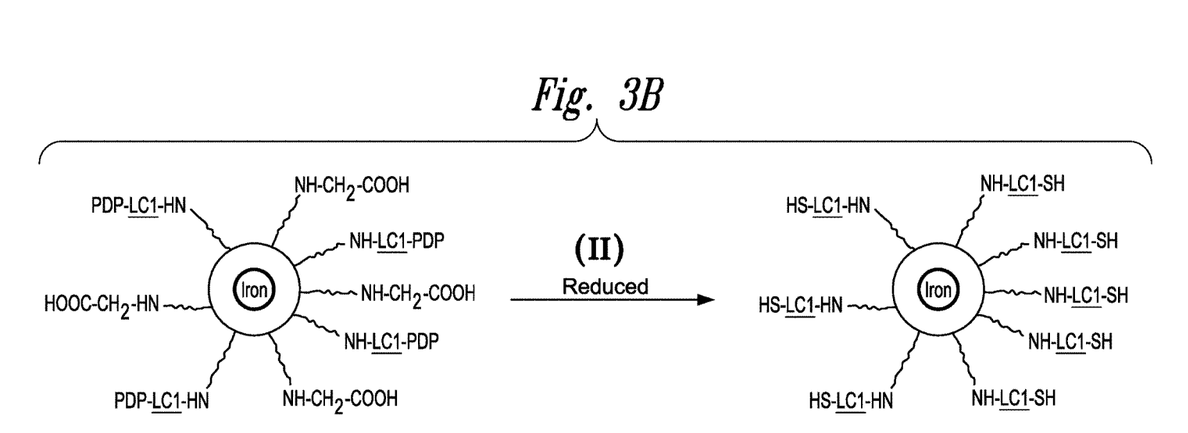
FIG. 3B depicts a reduction of the disulfide bond of PDP to provide a free SH group nanoparticle in accordance with an embodiment of the present invention.
Figure 3C:
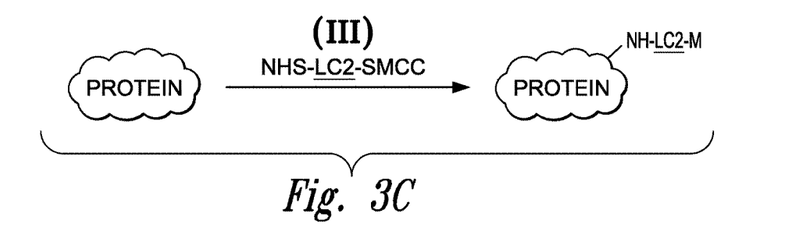
FIG. 3C depicts a reaction of long chain LC2-SMCC with the lysine groups of a protein nanoparticle in accordance with an embodiment of the present invention.
Figure 3D:
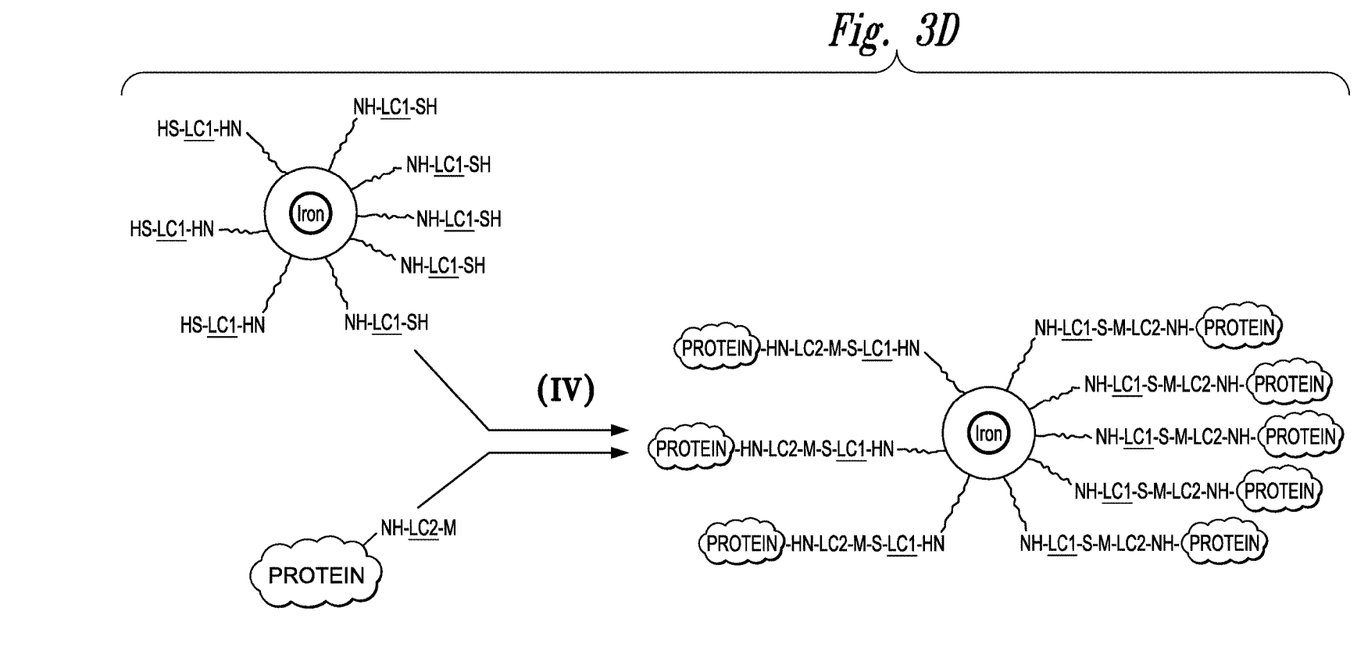
FIG. 3D depicts a reaction of a multifunctional nanoparticle with the protein that had been reacted with SMCC and contains a terminal reactive maleimide group nanoparticle in accordance with an embodiment of the present invention.

The peptide containing the LC-SMCC is treated with aminomercaptoethanol. This creates a linkage through the sulfhydryl group and provides a free amino group. This amino group is then coupled to the carboxyl group on the nanoparticle using EDC. EDC is known as 1-ethyl-3[3-dimethylaminopropyl]carbodiimide hydrochloride. This coupling step is performed last in the reaction scheme.

FIG. 1 shows the general description of the magnetic nanoparticles—protein/peptide adducts. The magnetic nanoparticle is coated with a polysaccharide and then functionalized. It can be purchased with amines on the surface. They can also be altered/morphed into any other functional formats. The extender/connector physically binds the two units together.

Various functional groups may be used to chemically attach the nanoparticle to the protein via crosslinking reactions. The variety of functional groups available does allow for numerous proteins/peptides to be attached to the nanoparticle, one step at a time.

Similarly, various crosslinking reagents or reactive catalysts may be used to crosslink nanoparticles with proteins/peptides via hetero-bifunctional reagents. It should also be noted that these crosslinking reagents come in various lengths. For instance many contain the LC notation, referring to extenders or "long chains". The pegylated compound is also available in various lengths. In this way linkers of various lengths may be added to the nanoparticles and provide differing attachment lengths for larger molecules, such as proteins and small molecules, such as peptides.

Often time different proteins may contain the same functional groups, making it difficult to label the nanoparticle with the various proteins. There are reagents which allow a change in functional groups; hence, we can change the functional groups on proteins, thus giving us the selectivity in a step wise fashion without interference from the other proteins. This requires changing the functional groups on proteins.

Various reagents can be used to alter proteins so that different chemistries may be used to attach proteins with like functional groups. For instance, a compound, such as SPDP, can be used to convert and amine to a sulfhydryl, which is then receptive towards reaction with a maleimide moiety.

When attaching proteins to the bead (nanoparticle) in a stepwise fashion, often residual and active groups of proteins that were attached previously may interfere with the coupling chemistries. Thus permanent or reversible capping reagents may be used to block these active moieties from interference with reagents that are about to be used to attach a second or third protein to the nanoparticle.

Numerous different capping compounds may be used to block the unreacted moiety. They need to be used judiciously as the capping compounds may also interfere with protein activity. Used most often when a second chemical attachment step is required and this functional group may interfere.

To show that proteins can be attached to beads (nanoparticles) using the chemistries noted above, we provided the synthesis of magnetic nanoparticles, which contained Green Fluorescent protein derived from Jelly fish. LCC-SMCC was used in this synthesis scheme.

The N-hyhroxysuccinimide is chemically reacted with the free amine groups on the nanoparticle in order to form a chemical bond. This provides a maleimide end group that can react with GFP. It is known that GFP has two cysteines and the cysteines from various GFP molecules may react to form disulfide bonds. To remove such interference, the molecule is first reduced with Cleland's reagent.

The protein is purified and then allowed to react with beads containing the LC-maleimide group. The reaction is allowed to proceed for 1 hour and reaction purified on Amicon spin filter (50K cutoff). Pictures were taken on the fluorescence electron microscope.

Multiple types of functional groups can be created on a nanoparticle. This allows the addition of three or more different proteins to be attached.

One first starts out with an amine on the surface.

Traut's reagent may be used to convert some of those amines to sulfhydryl. In addition iodoacetic acid may be used to convert some amines to carboxylic acid For both proteins and peptides, the amines are converted to the functional groups with different linker length as described in more detail below. This will serve as a generalized group to attach proteins and peptides.

FIG. 1 depicts schematic representation of nanoparticle functionalization and binding of peptides and proteins to nanoparticle.

The syntheses and coating are performed as follows: NHS-LC-SPDP commercially available through Thermo Fisher is a long chain extender with bifunctional coupling reagents on either side, which are specific for amines and a disulfide that can be converted to a sulfide.

One end has an N-Hydroxysuccinimide ester, while the other end of the extender contains a pyridyldithiol group. This dithiol group can be reduced to produce a sulfhydryl. NHS-LC-SPDP is allowed to react with the nanoparticles and the reaction can be cleared from unincorporated NHS-LC-SPD. The coupled nanoparticles are then reduced as shown in FIG. 1.

Production of Coupled Proteins: The biologically active proteins purified using affinity columns contain a free epsilon-amine group from carboxy-terminal lysine residue added to facilitate binding to the nanoparticles. NHS-LC-SMCC is used as the bifunctional coupling reagent. The molecule has an LC1 chain extender. One end has the N-Hydroxysuccinimide reagent specific for amines The other end contains the maleimide group, very specific for sulfhydryl groups. Once the material is coupled to a protein and separated from the reaction mixture, the maleimide coupled protein will be added to the sulfhydryl containing nanoparticle. The resultant material s separated by gel filtration.

Peptide Coupling to Nanoparticle: In this case the peptide also contains a carboxy-terminal lysine that will serve as the base for the NHS ester-LC-maleimide coupling. The molecule has an LC2 chain extender. All procedures are similar to those describe above for the protein.

During the optimization, the membrane-permeable peptide and the proteins will be mixed at different ratios to achieve the maximum number of molecules coupled to nanoparticle. Based on previously published studies, 3-4 molecules of surface-bound cell-penetrating peptide per nanoparticle are sufficient for efficient intracellular delivery of superparamagnetic nanoparticles.

The use of LC2-extender arm provides an important means to increase the number of bound peptide-based molecules. The use different concentration of NHS-LC-SPDP allows increased number of anchored peptide and protein molecule to the surface of nanoparticles, and therefore, more efficient penetration and consequently, more robust cell reprogramming activity.

Attachment of Peptides and Proteins on One Nanoparticle: This may be accomplished using the procedure shown in FIG. 1. In this case, ratios of SMCC labeled proteins and peptides are added to the beads and allowed to react.

Another more direct and controlled means of labeling a nanoparticle with a peptide and protein would be to use two different bifunctional coupling reagents (FIGS. 2A-F). The reaction sequence is somewhat similar to that of FIG. 1 with some modifications described below.

Iodoacetic acid is used to introduce a select number of "carboxyl" groups on the nanoparticle surface. This is performed at step I; see FIGS. 2A-F, steps (I-VII).

The peptide containing the NH-LC-SMCC is treated with aminoethanol. This creates a linkage through the sulfhydryl group and provides a free amino group. This amino group is then coupled to the carboxyl group on the nanoparticle using EDAC (EDC). EDAC is known as 1-ethyl-3[3-dimethylaminopropyl]carbodiimide hydrochloride. This coupling step is performed last in the reaction scheme.

In another aspect, the present invention is also directed to a method of delivering bioactive molecules attached to functionalized nanoparticles for modulation of intracellular activity. For example, human cells, fibroblasts or other cell types that are either commercially available or obtained using standard or modified experimental procedures are first plated under sterile conditions on a solid surface with or without a substrate to which the cells adhere (feeder cells, gelatin, martigel, fibronectin, etc.). The plated cells are cultured for a time with a specific factor combination that allows cell division/proliferation or maintenance of acceptable cell viability. Examples are serum and/or various growth factors, which can later be withdrawn or refreshed and the cultures continued. The plated cells are cultured in the presence of functionalized biocompatible cell-permeable nanoparticles with bioactive molecules attached using various methods described herein in the presence or absence of magnetic field. The use of a magnet in case of superparamagnetic nanoparticles renders an important increase in the contact surface area between the cells and nanoparticles and thereby reinforces further improved penetration of functionalized nanoparticles through the cell membrane. When necessary, the cell population is treated repeatedly with the functionalized nanoparticles to deliver the bioactive molecules intracellularly.

The cells are suspended in culture medium, and non-incorporated nanoparticles are removed by centrifugation or cell separation, leaving cells that are present as clusters. The clustered cells are then resuspended and recultured in fresh medium for a suitable period. The cells can be taken through multiple cycles of separating, resuspending, and reculturing, until a consequent biological effect triggered by the specific bioactive molecules delivered intracellularly is observed.

One use of the invention is the screening of a compound (or compounds) for an effect on cell reprogramming. This involves combining the compound attached to the nanoparticle using one or more of the methods in disclosed herein with a cell population of interest, culturing for suitable period and then determining any modulatory effect resulting from the compound(s). This may include initiation of the cell reprogramming and generation of pruripotent stem cells, differentiation or transdifferentiation of cells to more specialized or different specialized cell types, examination of the cells for toxicity, metabolic change, or an effect on contractile activity and other functions.

Another use of the invention is the formulation of specialized cells as a medicament or in a delivery device intended for treatment of a human or animal body. This enables the clinician to administer the cells in or around the damaged tissue (whether heart, muscle, liver, etc.) either from the vasculature or directly into the muscle or organ wall, thereby allowing the specialized cells to engraft, limit the damage, and participate in regrowth of the tissue's musculature and restoration of specialized function.

A use of the present invention involves nanoparticles functionalized with other proteins such as Oct4 and Sox2 transcription factors so as to ensure cell reprogramming and generation of stem or more differentiated cell types with preservation of intact genome.

Another use of the present invention is the screening of a compound (or compounds) for an effect on cell reprogramming. This involves combining the compound attached to the nanoparticle using the methods disclosed herein with a cell population of interest, culturing for suitable period and then determining any modulatory effect resulting from the compound(s). This may include initiation of the cell reprogramming and generation of pluripotent stem cells, differentiation or transdifferentiation of cells to more specialized or different specialized cell types, examination of the cells for toxicity, metabolic change, or an effect on contractile activity and other functions.

Still another use of the present invention is the formulation of specialized cells as a medicament or in a delivery device intended for treatment of a human or animal body. This enables the clinician to administer the cells in or around the damaged tissue (whether heart, muscle, liver, etc) either from the vasculature or directly into the muscle or organ wall, thereby allowing the specialized cells to engraft, limit the damage, and participate in regrowth of the tissue's musculature and restoration of specialized function.

As way of further illustration and not limitation, the following Examples disclose other aspects of the present invention.

EXAMPLES

Example 1

GFP was linked to the superparamagnetic particle using LC-SMM as the crosslinker (attached to the amine groups of the beads) which was then coupled directly to the sulhydryl groups on GFP. LC-SMCC (from Thermo Fisher) was dissolved in dimethylformamide (DMF) obtained from ACROS (sealed vial and anhydrous) at the 1 mg/ml concentration. Sample was sealed and used almost immediately.

Ten (10) microliters of the solution was added to nanoparticles in 200 microliter volume. This provided a large excess of SMCC to the available amine groups present, and the reaction was allowed to proceed for one hour. Excess SMCC and DMF was removed using an Amicon spin filter with a cutoff of 3,000 daltons. Five exchanges of volume were required to ensure proper buffer exchange. It was important that excess of SMCC be removed at this stage.

Any peptide based molecule, as an example commercially available Green Fluorescent Protein (GFP) or purified recombinant GFP or other proteins) were added to the solution containing a certain amount of ethylene glycol for freezing at −30° C. To 3 micrograms of the protein in 14 microliters, 10 microliters of a freshly prepared DTT (dithiothreitol, Cleland's reagent) solution in PBS were added with vigorous vortexing. Because the proteins usually contain more than one cysteine, there was a tendency to crosslink different GFP molecules. Therefore, the excess DTT reduced the dithiol linkage and freed the GFP. Reaction was allowed to proceed for two hours at 4° C. and then excess reagent was removed by an Amicon centrifugal filter unit with a 3,000 MW cutoff.

The activated nanoparticles and the protein solutions were combined and allowed to react for two hours, after which the unreacted protein was removed by an Amicon centrifugal filter unit having an appropriate MW cutoff (in the example with GFP it is 50,000 dalton cut-off). Sample was stored at −80° C. It should also be noted that a sulfo derivative of SMCC (Sulfo-SMCC), which is more water soluble, can be used. DMSO may also be substituted for DMF as the solvent carrier for the labeling reagent; again, it should be anhydrous.

Example 2

In this method the amino groups of lysine were used for the coupling reaction to sulhydryl groups on the bead. Beads freshly equilibrated with 0.1 M phosphate buffer at pH 7.2, were used in these studies. LC-SPDP at 1 mg/ml (in DMF) was freshly prepared. 10 microliters of SPDP solution was added to the bead suspension under vigorous vortexing and allowed to react for one hour. Subsequently, the unreacted material was removed by centrifugation and the nanoparticles washed with phosphate buffer using an Amicon Spin filter with a 10K cutoff. The disulfide bond of SPDP was broken using Clelands reagent; 1 mg was added to the solution and the reaction allowed to proceed for one hour. Byproducts and unreacted Clelands reagent were removed via an Amicon spin filter with a 10K cutoff.

While the above reaction proceeded, GFP was blocked using N-ethylmaleimide. Excess ethylmaleimide was added to the GFP solution. Reaction proceeded for one hour at room temperature and unwanted materials removed using an Amicon Spin filter with a 3K cutoff. The GFP was then allowed to react with excess SMCC for one hour. Subsequently, GFP was purified on a spin column and then reacted with PDP-nanoparticles. Reaction proceeded for one hour and the final product purified using an Amicon spin filter with a cutoff of 50K.

Example 3

Human fibroblasts commercially available or obtained using standard experimental procedures as described [Moretti et al., Mouse and human induced pluripotent stem cells as a source for multipotent Is11 cardiovascular progenitors. FASEB J. 24:700 (2010)] are plated at 150,000 cells density under sterile conditions on a solid surface with or without preplated feeder cells at 150,000-200,000 density in six-well plates. The feeder cells obtained either commercially or using standard laboratory procedures. The plated cells are cultured for some time with a specific factor combination that allows cell division/proliferation or maintenance of acceptable cell viability in serum-containing culture medium, which can later be withdrawn or refreshed and the cultures continued under sterile conditions in a humidified incubator with 5% $CO_2$ and ambient $O_2$.

The cells collected at the bottom of a conical tube or the plated cells are treated with 50 microliters of suspension containing functionalized biocompatible cell-permeable nanoparticles with bioactive molecules attached using various methods disclosed herein in the presence or absence of magnetic field.

The use of magnetic field in case of superparamagnetic nanoparticles renders an important increase in the contact surface area between the cells and nanoparticles and thereby ensuring improved penetration of functionalized nanoparticles through the cell membrane. Importantly, similar to poly(ethylene glycol) PEG-mediated protection of several protein-based drugs (PEG-GCSF, Amgen, Calif.; PEG-Interferon, Schering-Plough/Merck, NJ) to which PEG is attached, the nanoparticles used in conjunction with coupled peptides increase the size of the polypeptide and masks the protein's surface, thereby reducing protein degradation by proteolytic enzymes and resulting in a longer stability of the protein molecules used. If necessary, the cell population is treated repeatedly with the functionalized nanoparticles to deliver the bioactive molecules intracellularly.

The cells are suspended in culture medium, and non-incorporated nanoparticles are removed by centrifugation for 10 minutes at approximately 1200×g, leaving cells that are present as clusters in the pellet. The clustered cells are then resuspended, washed again using similar procedure and recultured in fresh medium for a suitable period. The cells can be taken through multiple cycles of separating, resuspending, and reculturing in a culture media until a consequent biological effect triggered by the specific bioactive molecules delivered intracellularly is observed.

In this specific example with green fluorescent protein, the cell-penetrant nanoparticles deliver the protein inside the cells, which confers acquisition of novel green fluorescence by the target cells. This newly acquired property allows subsequent sorting and separation of the cells with intracellularly delivered protein to high degree of homogeneity that can be further used for various applications. Importantly, the use of cell-permeable functionalized nanoparticles with attached protein devoid any integration into the cell genome, thereby ensuring that every cell with novel (in this case fluorescent) property maintains intact genome and preserves the integrity of cellular DNA.

The present invention may be embodied in other specific forms without departing from the spirit or essential characteristics thereof. The foregoing embodiments are therefore to be considered illustrative rather than limiting of the invention described herein. The scope of the invention is thus indicated by the appended claims rather than by the foregoing description, and all changes that come within meaning and range of equivalency of the claims are intended to be embraced herein.

What is claimed is:

1. A functionalized biocompatible nanoparticle for penetrating through a mammalian cell membrane and delivering intracellularly a bioactive molecule for modulating a cellular function, said functionalized biocompatible nanoparticle comprising:
   a central nanoparticle having one or more functional groups attached thereto,
   a cell penetrating peptide for penetrating through a membrane of said mammalian cell, wherein said cell penetrating peptide is attached via a first linker molecule to a first functional group on said central nanoparticle, and
   a bioactive molecule for modulating a function of said mammalian cell, wherein said bioactive molecule is attached via a second linker molecule to a second functional group on said central nanoparticle;
   wherein said cell penetrating peptide and said bioactive molecule are independently attached to said central nanoparticle via attachment of said cell penetrating peptide to said first linker molecule and attachment of said bioactive molecule to said second linker molecule.

2. The functionalized biocompatible nanoparticle of claim 1 wherein said central nanoparticle has a size ranging from 5 to 50 nm.

3. The functionalized biocompatible nanoparticle of claim 1 wherein said first functional group is the same as said second functional group.

4. The functionalized biocompatible nanoparticle of claim 1 wherein said central nanoparticle further comprises a polymer coating.

5. The functionalized biocompatible nanoparticle of claim 4 wherein one or both of said first functional group and said second functional group are attached to said polymer coating on said central nanoparticle.

6. The functionalized biocompatible nanoparticle of claim 1 wherein said central nanoparticle comprises iron.

7. The functionalized biocompatible nanoparticle of claim 1 wherein said first linker molecule has a first length, wherein said second linker molecule has a second length, and wherein said first length is greater than said second length.

8. The functionalized biocompatible nanoparticle of claim 1 wherein said cell penetrating peptide includes from five basic amino acids to nine basic amino acids.

9. The functionalized biocompatible nanoparticle of claim 1 wherein said cell penetrating peptide includes nine or more basic amino acids.

10. The functionalized biocompatible nanoparticle of claim 1 wherein said bioactive molecule is a transcription factor.

11. The functionalized biocompatible nanoparticle of claim 10 wherein said transcription factor is selected from the group consisting of Oct4, Sox2, Nanog, Lin28, cMyc, and Klf4.

12. A method for changing a cellular functionality of a mammalian cell, said method comprising contacting a mammalian cell with a functionalized biocompatible nanoparticle of claim 1 thereby changing a cellular functionality of said mammalian cell.

13. The method of claim 12 wherein said change in cellular functionality of said mammalian cell is selected from the group consisting of a change in a physico-chemical property of said mammalian cell, a change in a proliferative property of said mammalian cell, a change in survivability of said cell, a change in a morphological property of said mammalian cell, and a change in the differentiation state of said mammalian cell.

14. The method of claim 13 wherein said change in the differentiation state of said mammalian cell comprises the conversion of said mammalian cell into a stem cell.

* * * * *